(12) United States Patent
Wang et al.

(10) Patent No.: US 10,422,785 B2
(45) Date of Patent: Sep. 24, 2019

(54) TISSUE IDENTIFICATION METHOD AND BIOSENSOR FOR TISSUE IDENTIFICATION

(71) Applicant: National Tsing Hua University, Hsinchu (TW)

(72) Inventors: Yu-Lin Wang, Hsinchu (TW); Indu Sarangadharan, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 542 days.

(21) Appl. No.: 15/137,787

(22) Filed: Apr. 25, 2016

(65) Prior Publication Data
US 2017/0241928 A1     Aug. 24, 2017

(30) Foreign Application Priority Data
Feb. 23, 2016   (TW) .............................. 105105217 A

(51) Int. Cl.
```
G01N 27/02      (2006.01)
G01N 33/483     (2006.01)
G01N 27/414     (2006.01)
```
(52) U.S. Cl.
CPC ..... G01N 33/4833 (2013.01); G01N 27/4146 (2013.01)

(58) Field of Classification Search
CPC ........... G01N 27/4145; G01N 27/414–27/417; G01N 27/4167; G01N 27/4117; G01N 27/4035; G01N 27/301; G01N 27/302
See application file for complete search history.

(56) References Cited

U.S. PATENT DOCUMENTS

| 5,807,261 A | 9/1998 | Benaron et al. |
| 7,759,710 B1 | 7/2010 | Chiu et al. |

(Continued)

FOREIGN PATENT DOCUMENTS

| CN | 102483369 | 5/2012 |
| CN | 103932797 | 10/2015 |

(Continued)

OTHER PUBLICATIONS

Chang-Soo Lee, et al., "Ion-Sensitive Field-Effect Transistor for Biological Sensing," Sensors, vol. 9, Sep. 7, 2009, pp. 7111-7131.

(Continued)

*Primary Examiner* — Gurpreet Kaur
(74) *Attorney, Agent, or Firm* — J.C. Patents

(57) ABSTRACT

A tissue identification method including a preparation step and a detection step is provided. The preparation step includes preparing a biosensor which includes a transistor and a response electrode. The response electrode is spaced apart from the transistor relative to a gate terminal of the transistor. The detection step includes disposing a biological tissue sample to be identified on the response electrode, applying a pulse voltage that has a tunable pulse width and a tunable pulse height to the response electrode, resulting in a voltage difference between the response electrode and the gate terminal of the transistor, and measuring and calculating a detection current which is generated from the transistor in the pulse width, so as to obtain a first sensing indicator. In addition, a biosensor for tissue identification is also provided.

10 Claims, 6 Drawing Sheets

(56) References Cited

U.S. PATENT DOCUMENTS

| | | | |
|---|---|---|---|
| 2008/0063566 A1* | 3/2008 | Matsumoto | G01N 33/5438 422/68.1 |
| 2010/0071100 A1* | 3/2010 | Faris | B81B 1/006 850/57 |
| 2011/0180856 A1* | 7/2011 | Ahn | G01N 27/4145 257/253 |

FOREIGN PATENT DOCUMENTS

| | | |
|---|---|---|
| TW | I267637 | 12/2006 |
| TW | I364539 | 5/2012 |

OTHER PUBLICATIONS

"Office Action of Taiwan Counterpart Application," dated Dec. 16, 2016, p. 1-p. 5.

* cited by examiner

TISSUE IDENTIFICATION METHOD AND BIOSENSOR FOR TISSUE IDENTIFICATION

CROSS-REFERENCE TO RELATED APPLICATION

This application claims the priority benefit of Taiwan application serial no. 105105217, filed on Feb. 23, 2016. The entirety of the above-mentioned patent application is hereby incorporated by reference herein and made a part of this specification.

BACKGROUND OF THE INVENTION

Field of the Invention

The invention relates to a tissue identification method and a biosensor for tissue identification, and particularly relates to a biological tissue identification method and a biosensor for biological tissue identification.

Description of Related Art

In the development of medical profession, surgical medical operation is one of the important treatment methods, especially in the treatment of tumor or cancer patients, surgical resection of tumor is the most basic and effective treatment method.

Specifically, in the field of the surgical medical operation, tissue identification is very important for the success rate and safety of the surgical operation. In the past, it was often difficult for surgeons to accurately distinguish between tumor tissue and healthy tissue at the moment of the surgical operation. However, in the process of the surgical operation, if the surgeons want to send the slice for pathological examination, it takes at least 30 minutes or so to know the results of tissue identification. Additionally, in the prior art, although an endoscope and other equipment can be used for assistance, the surgeons may still need to judge by clinical experience. As a result, it may be difficult to effectively and safely perform the surgical operation, resulting in reducing accuracy of the resection of tumor tissue, thereby increasing the likelihood of disease recurrence. Also, it may cause adverse effects on the survival rate of patients. Furthermore, it is possible that the tumor tissue may not be completely resected, such that the surgical operation is required to be performed at the original surgical site again, so as to increase the number of the surgical operation resulted burdens of patients.

On the other hand, when the surgeons perform normal resection operation, in the case of failure to accurately identify blood vessels and tissues surrounding blood vessel, the blood vessels may be accidentally touched or miscut, causing unnecessary bleeding. If the bleeding situation is serious, it may even endanger the lives of patients, thereby increasing the risk of the surgical medical operation.

Based on the above, a method which identifies and distinguishes tissue effectively and rapidly is urgently needed, such that the surgical medical operation can be performed more effectively and safely.

SUMMARY OF THE INVENTION

The invention provides a tissue identification method which identifies and distinguishes tissue more effectively, simply and rapidly, such that the surgical medical operation can be performed more effectively and safely.

The invention also provides a biosensor for tissue identification which can be used for the above tissue identification method.

A tissue identification method of the invention includes a preparation step and a detection step. The preparation step includes preparing a biosensor which includes a transistor and a response electrode. The response electrode is spaced apart from the transistor relative to a gate terminal of the transistor. The detection step includes disposing a biological tissue sample to be identified on the response electrode, applying a pulse voltage which has a tunable pulse width and a tunable pulse height to the response electrode, resulting in a voltage difference between the response electrode and the gate terminal of the transistor, and measuring and calculating a detection current which is generated from the transistor in the pulse width so as to obtain a first sensing indicator.

According to an embodiment of the invention, the tissue identification method further includes performing a transform step after the detection step, wherein an integral transform is performed on the detection current with respect to the pulse width so as to obtain a second sensing indicator.

According to an embodiment of the invention, the tissue identification method further includes performing a transform step after the detection step, wherein a value of the detection current corresponding to the pulse width is divided by a maximum value of the detection current, and an integral transform is performed on the pulse width so as to obtain a third sensing indicator.

According to an embodiment of the invention, the transistor includes a high electron mobility transistor, a Si-based field-effect transistor, a nanowire field-effect transistor, a carbon nanotube field-effect transistor, a graphene field-effect transistor, or a molybdenum disulfide field-effect transistor.

According to an embodiment of the invention, the response electrode is spaced apart on the gate terminal of the transistor.

According to an embodiment of the invention, the response electrode is disposed on a substrate of the transistor, and the response electrode and the gate terminal of the transistor are arranged in a coplanar manner.

According to an embodiment of the invention, a source of the biological tissue sample includes muscles, blood vessels, tissues surrounding blood vessels, fats, viscera, or tumor tissues.

A biosensor for tissue identification of the invention includes a transistor having a gate terminal and a response electrode. The response electrode is spaced apart from the transistor relative to the gate terminal of the transistor. A biological tissue sample to be identified is disposed on the response electrode. When a voltage is applied to the response electrode, a voltage difference is generated between the response electrode and the gate terminal of the transistor.

According to an embodiment of the invention, the transistor includes a high electron mobility transistor, a Si-based field-effect transistor, a nanowire field-effect transistor, a carbon nanotube field-effect transistor, a graphene field-effect transistor, or a molybdenum disulfide field-effect transistor.

According to an embodiment of the invention, the response electrode is spaced apart on the gate terminal of the transistor.

According to an embodiment of the invention, the response electrode is disposed on a substrate of the transistor, and the response electrode and the gate terminal of the transistor are arranged in a coplanar manner.

According to an embodiment of the invention, a source of the biological tissue sample includes muscles, blood vessels, tissues surrounding blood vessels, fats, viscera, or tumor tissues.

Based on the above, the tissue identification method can be performed by the high electron mobility transistor (HEMT). The high electron mobility transistor has advantages of good electrical property, chemical stability, biological compatibility, thermal stability, and low power consumption. Therefore, the method for tissue identification by the field-effect transistor of the invention can identify and distinguish tissue more effectively, simply, and rapidly, so as to prevent doctors from miscutting blood vessels during the surgical operation. Also, it can prevent damage of normal tissue and resect the tumor tissue more effectively during the tumor tissue resection operation, thereby improving the efficiency and safety of the surgical medical operation.

In order to make the aforementioned features and advantages of the disclosure more comprehensible, embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
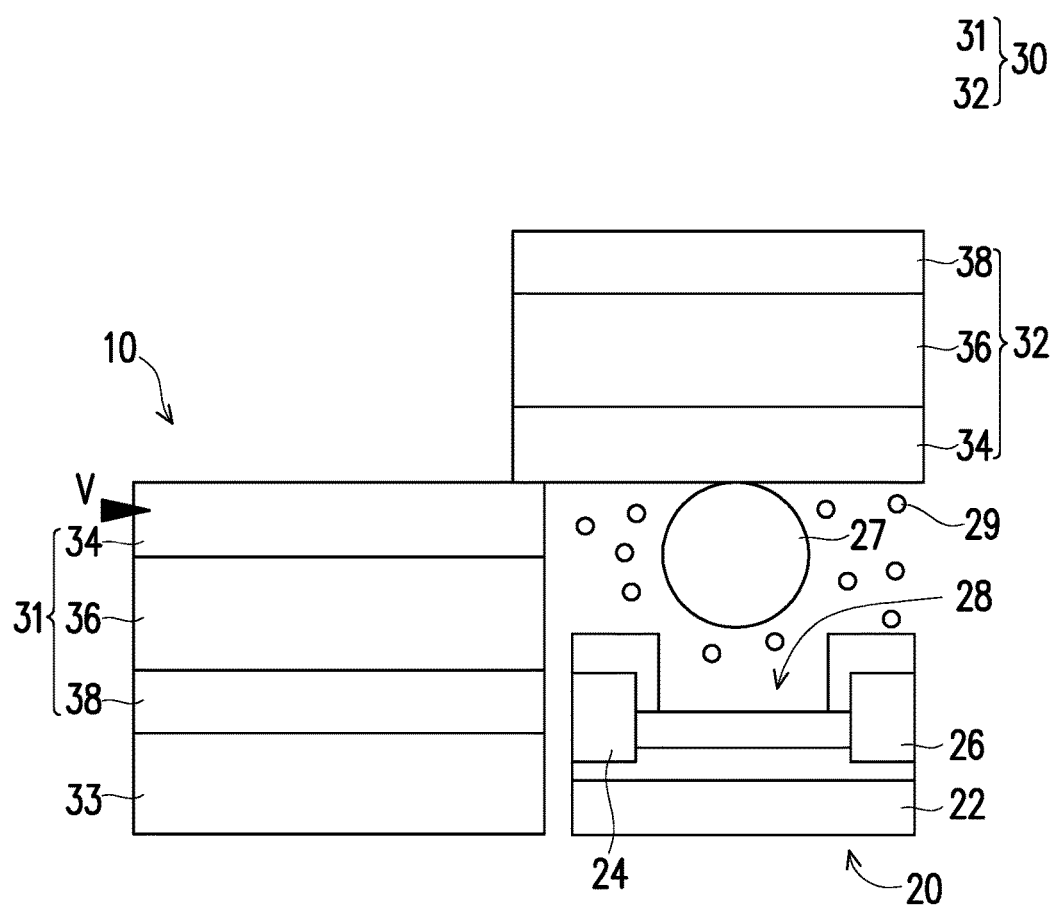
FIG. 1 is a schematic side view of a biosensor for tissue identification according to a first embodiment of the invention.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

FIG. 1 is a schematic side view of a biosensor for tissue identification according to a first embodiment of the invention.

Referring to FIG. 1, a biosensor 10 for tissue identification includes a transistor 20 and a response electrode 30.

As shown in FIG. 1, the transistor 20 may include a base body 22, a source terminal 24, a drain terminal 26, and a gate terminal 28 disposed between the source terminal 24 and the drain terminal 26.

Specifically, the transistor 20 which is suitable for the biosensor 10 of the invention may include a high electron mobility transistor, a carbon nanotube field-effect transistor, a graphene field-effect transistor, or a molybdenum disulfide field-effect transistor. However, the invention is not limited thereto. The high electron mobility transistor is used as an example to illustrate in the present embodiment, and the structure is that a gallium nitride (GaN) layer and an aluminum indium nitride (AlInN) layer are sequentially formed on a sapphire substrate to obtain the base body 22, for example. Also, the source terminal 24, the drain ten final 26, and the gate terminal 28 are formed on the base body 22 by an exposure and development process to form the transistor 20. As the exposure and development process is known by a person skilled in the art and not the focus of the invention, details are not illustrated here.

The high electron mobility transistor is used in the present embodiment. Thus, the transistor 20 can have excellent carrier transport properties when applied to the biosensor mainly due to a low-dimensional heterostructure interface between AlInN/GaN. It should be noted that, the material of the layer formed on the gallium nitride layer is not limited to aluminum indium nitride, other materials having piezoelectric properties (e.g., aluminum gallium nitride (AlGaN)) may also be used.

Referring to FIG. 1, the response electrode 30 includes a response layer 34 located on a top surface, and the response layer 34 is composed of gold, for example. Specifically, the response layer 34 is spaced apart from the transistor 20 relative to the gate terminal 28 of the transistor 20, and the response layer 34 is disposed above the gate terminal 28 of the transistor 20. Besides, the response electrode 30 is not electrically connected with the gate terminal 28.

As shown in FIG. 1, the response electrode 30 of the present embodiment may be substantially composed of a first sub-electrode 31 and a second sub-electrode 32 with identical structure oppositely connected to each other. Specifically, in the first sub-electrode 31 and the second sub-electrode 32, a silicon nitride layer 36 is formed on a silicon substrate 38, and then the response layer 34 is formed on the silicon nitride layer 36, for example. As a result, the silicon nitride layer 36 blocks electrons generated in the subsequent biological detection in the response layer 34 from transferring to the silicon substrate 38, thereby reducing the measured error values.

In the present embodiment, the first sub-electrode 31 is disposed on a glass substrate 33 in a direction that the response layer 34 is away from the silicon substrate 38, for example, and a sum of heights of the first sub-electrode 31 and the glass substrate 33 is greater than a height of the transistor 20. After that, the response layer 34 of the second sub-electrode 32 and the response layer 34 of the first sub-electrode 31 are connected to each other, and the response layer 34 of the second sub-electrode 32 is protruded from the first sub-electrode 31. Thus, the response layer 34 of the second sub-electrode 32 is located above the gate terminal 28 of the transistor 20, and a gap space is formed between the response layer 34 of the second sub-electrode 32 and the gate terminal 28.

It should be noted that, the method of forming the response electrode 30 is not limited to the above structure. The response electrode 30 can be formed by an integrally-forming method depending on the circumstances.

Figure 2:
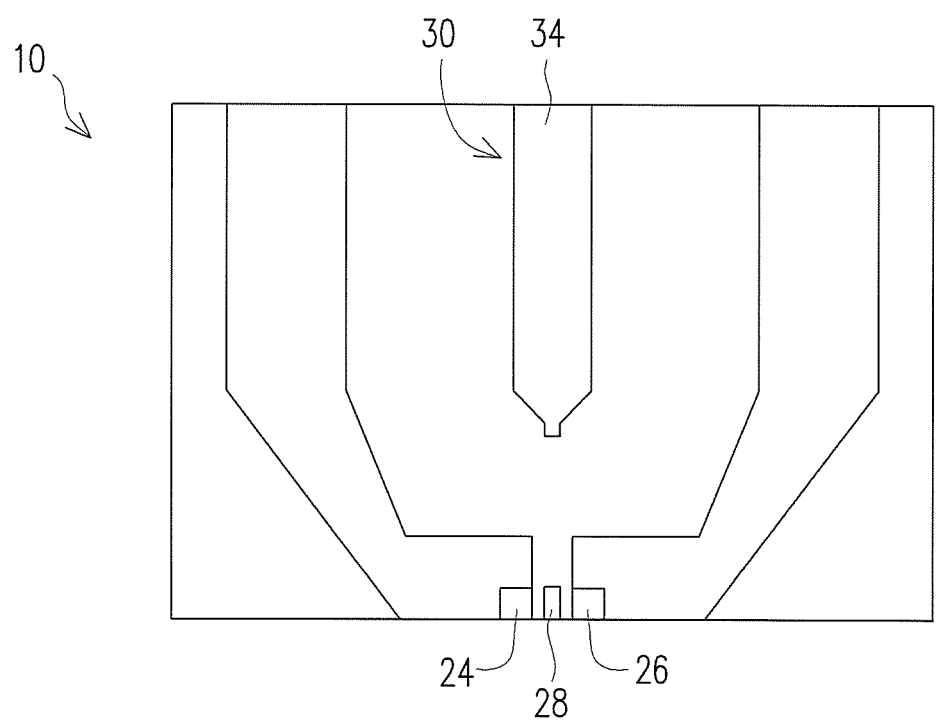
FIG. 2 is a schematic top view of a biosensor for tissue identification according to a second embodiment of the invention.

FIG. 2 is a schematic top view of a biosensor for tissue identification according to a second embodiment of the invention. The second embodiment as shown in FIG. 2 is similar to the first embodiment as shown in FIG. 1. Thus, the same components are represented by the same reference numbers, and are not repeated again here.

Referring to FIG. 2, the layer structure and the composition material of the second embodiment are approximately the same as the above first embodiment. The difference between the present embodiment and the above first embodiment is that, the response electrode 30 and the gate terminal 28 of the transistor 20 are arranged in a coplanar manner, and an aluminum gallium nitride (AlGaN) layer is formed on the gallium nitride (GaN) layer of the transistor 20. Specifically, in the present embodiment, by extending the substrate of the transistor 20 and disposing the response electrode 30 on the substrate, the response electrode 30 and the gate terminal 28 of the transistor 20 can be arranged in a coplanar manner and disposed spaced apart relative to each other.

The invention also provides a tissue identification method performed by the biosensor 10 of the above first embodiment or the second embodiment, wherein the tissue identification method includes a preparation step and a detection step. The preparation step includes preparing the biosensor 10 as shown in FIG. 1 or FIG. 2. In the following, the tissue identification method of the invention is illustrated by the biosensor 10 as shown in FIG. 1.

Referring to FIG. 1, after the biosensor 10 is prepared, the detection step is performed. A biological tissue sample 27 to be identified is disposed on the response layer 34 of response electrode 30, and the biological tissue sample 27 is pressed to be fully contacted with the response electrode 30 in a presence of a liquid medium 29 between the response electrode 30 and the gate terminal 28 of the transistor 20. Then, a pulse voltage V that has a tunable pulse width and a tunable pulse height is applied to the response layer 34 of the response electrode 30, resulting in a voltage difference between the response electrode 30 and the gate terminal 28 of the transistor 20, and a detection current I which is generated from the transistor 20 is measured and calculated in the pulse width so as to obtain a first sensing indicator generated from the biological tissue sample 27. After the first sensing indicator is obtained, the biological tissue sample 27 is removed. The biosensor is sequentially washed by PBST (PBS+Tween 20, wherein PBS is phosphate buffered saline) and deionized water.

Specifically, the biological tissue sample to be identified is cut into slices in a thickness of about 2.5 mm for the detection, for example. However, the invention is not limited thereto. The size of the biological tissue sample can be adjusted according to the actual operation situation, as long as the first sensing indicator can be generated by the biosensor of the invention. Additionally, the pulse width and the pulse height of the applied pulse voltage V can be adjusted according to the detection time desired to be analyzed by users and the required voltage of the detection, such as:

Single pulse: drain voltage=2 V; gate voltage=0.5 V; gate pulse width=0.5 µs

Biphasic pulse: drain voltage=2 V; gate voltage=0.5 V; gate cycle pulse width=1 ms It should be noted that, a transform step can be performed after the detection step, wherein the detection current I of the first sensing indicator is transformed to obtain other sensing indicators. The first transform method is that, an integral transform is performed on the detection current I with respect to the pulse width (t). At this time, the current is integrated with respect to time to obtain an amount of charge, thereby obtaining a total amount of charge accumulated from the source terminal 24 of the transistor 20 for a given period of time, which is used as a second sensing indicator. The second transform method is that, the detection current I corresponding to the pulse width (t) is divided by a maximum value of the detection current $I_{peak}$ to obtain dynamic current value P(t). Then, an integral transform is performed on the dynamic current value P(t) with respect to the pulse width (t) to obtain a time constant, which is used as a third sensing indicator.

In the invention, a source of the biological tissue sample to be identified may include muscles, blood vessels, tissues surrounding blood vessels, fats, viscera, or tumor tissues. The muscles are skeletal muscles, for example. The blood vessels are renal blood vessels, for example. However, the invention is not limited thereto. Other types of biological tissue can be used for identification according to the actual needs. The biological tissue samples from different parts of the body have different structures and compositions, and therefore induce different electrical responses. As a result, the detection is performed on different biological tissue samples by the above tissue identification method of the invention, and different first sensing indicators can be obtained so as to identify and distinguish different tissues. For example, renal blood vessels and tissues surrounding renal blood vessels, fats and skeletal muscles, or healthy tissues and tumor tissues can be identified by the tissue identification method of the invention.

Since the tissue identification method of the invention identifies and distinguishes tissue more effectively, simply and rapidly, the tissue identification method can be applied to a field related to the surgical medical operation. That is, the biosensor of the invention can be used as an auxiliary tool for the surgical medical operation. For example, when the surrounding tissue resection surgical operation is performed before the hemostasis of renal blood vessels, the biosensor can be installed in a probe head, and then the probe is slowly penetrated into the muscles near the kidney. When the probe touches the blood vessels, different signals are emitted. At this time, the penetration of the probe is stopped, and then the surgical knife is cut down along the probe. As a result, the tissue identification method can prevent surgeons from miscutting blood vessels during the surgical operation. Also, it can prevent damage of normal tissue and resect the tumor tissue more effectively during the tumor tissue resection operation, thereby improving the efficiency and safety of the surgical medical operation.

Hereinafter, the tissue identification method and the characteristics thereof provided by the invention are illustrated in detail by experimental examples. However, the following experimental examples are not used to limit the invention. It should be noted that, a pig biological tissue sample is used in the following experimental examples; however, the invention is not limited thereto. The tissue identification method provided by the invention can be applied to any other organism with tissue identification requirements. For example, the tissue identification method provided by the invention can be applied to the tissue identification of human biological tissue samples.

EXPERIMENTAL EXAMPLES

In order to prove the tissue identification method provided by the invention can identify and distinguish tissue more effectively, simply and rapidly, the following experimental examples are conducted.

It should be noted that, since the process of the tissue identification method has been described in detail above, the description of some details are omitted for the sake of convenience to describe below.

Detection on the Biological Tissue Sample by the Tissue Identification Method

Example 1

The biosensor of the above first embodiment was prepared. Next, pig skeletal muscles were cut into slices in a thickness of about 2.5 mm as the biological tissue sample and disposed on the response electrode, and the skeletal muscle sample was pressed to be fully contacted with the response electrode. Then, the pulse voltage V that has a pulse width of 50 µs and a pulse height of 0.5 V was applied to the response electrode, and the detection current I which was generated from the transistor was measured and calculated in the pulse width so as to obtain the first sensing indicator generated from the skeletal muscle sample.

After the first sensing indicator was obtained, the skeletal muscle sample was removed. The biosensor was sequentially washed by PBST and deionized water. Then, pig fats were cut into slices in a thickness of about 2.5 mm as the biological tissue sample and disposed on the response electrode, and the fat sample was pressed to be fully contacted with the response electrode. Then, the pulse voltage V that has a pulse width of 50 µs and a pulse height of 0.5 V was applied to the response electrode, and the detection current I which was generated from the transistor was measured and calculated in the pulse width so as to obtain the first sensing indicator generated from the fat sample.

Data Analysis

Figure 3:
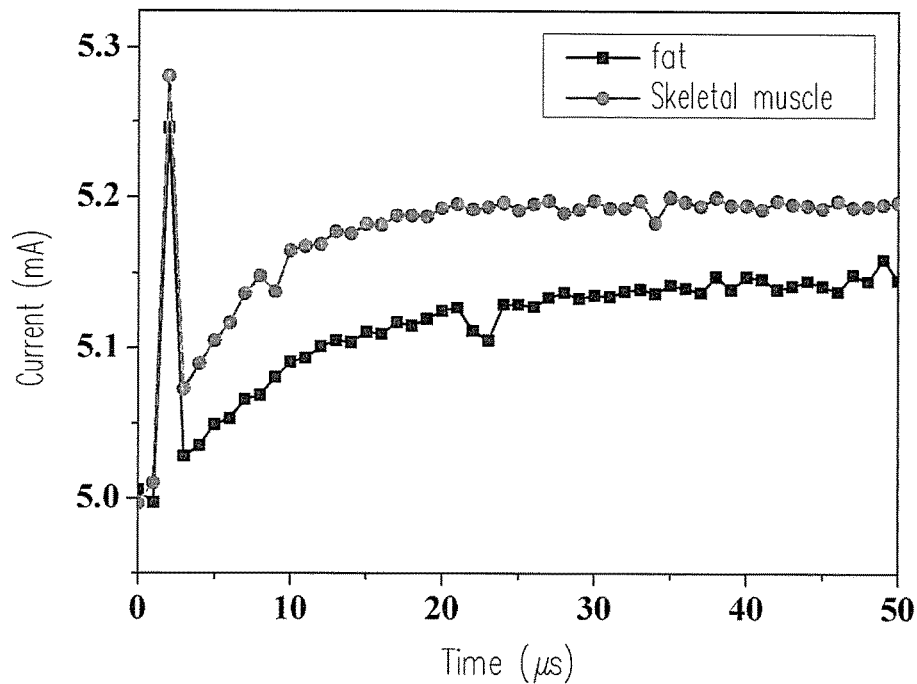
FIG. 3 is a diagram illustrating the relationship between current and time obtained from the detection of the skeletal muscle sample and the fat sample by the tissue identification method of the invention in Example 1.
Figure 4:
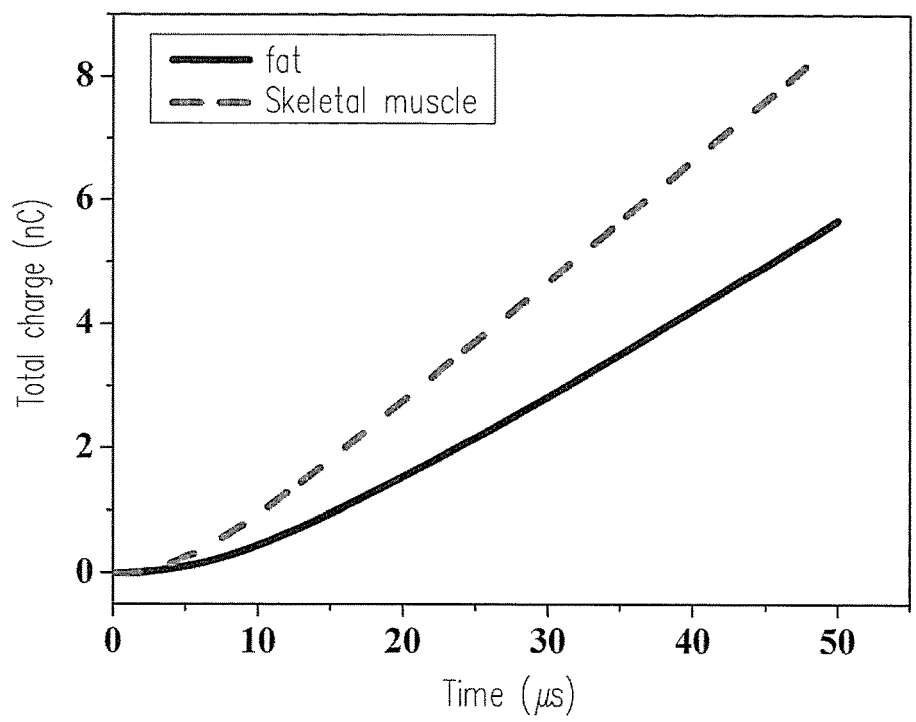
FIG. 4 is a diagram illustrating the relationship between charge and time of Example 1, so as to illustrate a curve diagram of current being integrated with respect to time of FIG. 3.
Figure 5:
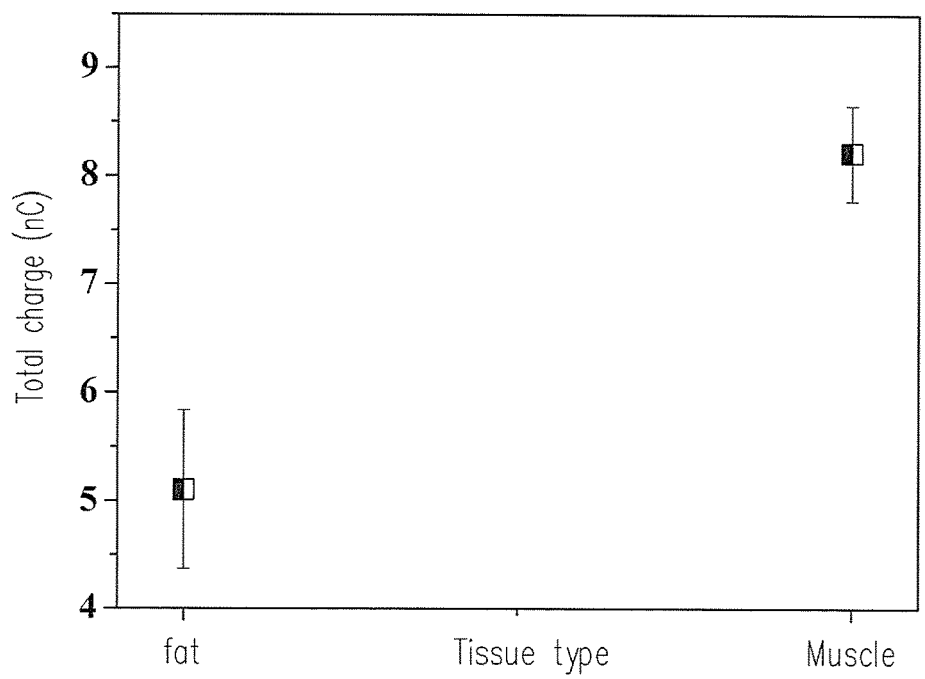
FIG. 5 is a diagram illustrating the relationship between specific time and charge of Example 1, so as to assist in illustrating the charge value at 50 µs of FIG. 4.

FIG. 3 is a diagram illustrating the relationship between current and time obtained from the detection of the skeletal muscle sample and the fat sample by the tissue identification method of the invention in Example 1. FIG. 4 is a diagram illustrating the relationship between charge and time of Example 1, so as to illustrate a curve diagram of current being integrated with respect to time of FIG. 3. FIG. 5 is a diagram illustrating the relationship between specific time and charge of Example 1, so as to assist in illustrating the charge value at 50 µs of FIG. 4.

Referring to FIG. 3, within a time period of 50 µs, the detection currents (first sensing indicators) of the skeletal muscle sample and the fat sample are significantly different. Thus, the tissue identification method provided by the invention can effectively, simply and rapidly identify and distinguish the skeletal muscle and the fat.

In addition to using the detection current I as the first sensing indicator, the second sensing indicator, in which the charge is used as an indicator, can be obtained by the transform step as described above.

Referring to FIG. 4, FIG. 4 shows a charge curve with respect to time obtained from an integral transform performed on each current value curve with respect to time of FIG. 3. From FIG. 4, within a time period of 50 µs, the total amounts of charge (second sensing indicators) of the skeletal muscle sample and the fat sample are significantly different. From the amount of charge being equal to the current times time (Q=I×t), it can be known that the amount of charge is proportional to the current. Thus, the charge curve shown in FIG. 4 conforms with the results of FIG. 3 in deed. Then, referring to FIG. 5, which shows the corresponding charge value at 50 µs for FIG. 4, the charge values of the skeletal muscle sample and the fat sample are significantly different.

Example 2

The biosensor of the above first embodiment was prepared. Next, pig renal blood vessels were cut into slices in a thickness of about 2.5 mm as the biological tissue sample and disposed on the response electrode, and the renal blood vessel sample was pressed to be fully contacted with the response electrode. Then, the pulse voltage V that has a pulse width of 50 µs and a pulse height of 0.5 V was applied to the response electrode, and the detection current I which was generated from the transistor was measured and calculated in the pulse width so as to obtain the first sensing indicator generated from the renal blood vessel sample.

After the first sensing indicator was obtained, the renal blood vessel sample was removed. The biosensor was sequentially washed by PBST and deionized water. Then, pig muscles surrounding renal blood vessels were cut into slices in a thickness of about 2.5 mm as the biological tissue sample and disposed on the response electrode, and the muscle surrounding renal blood vessel sample was pressed to be fully contacted with the response electrode. Then, the pulse voltage V that has a pulse width of 50 µs and a pulse height of 0.5 V was applied to the response electrode, and the detection current I which was generated from the transistor was measured and calculated in the pulse width so as to obtain the first sensing indicator generated from the muscle surrounding renal blood vessel sample.

Data Analysis

Figure 6:
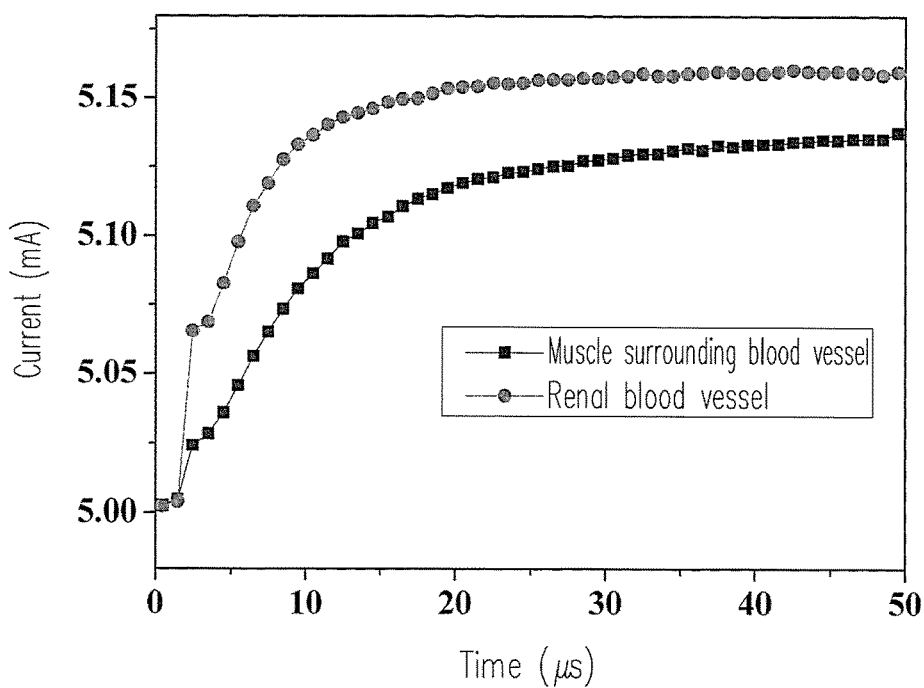
FIG. 6 is a diagram illustrating the relationship between current and time obtained from the detection of the renal blood vessel sample and the muscle surrounding renal blood vessel sample by the tissue identification method of the invention in Example 2.
Figure 7:
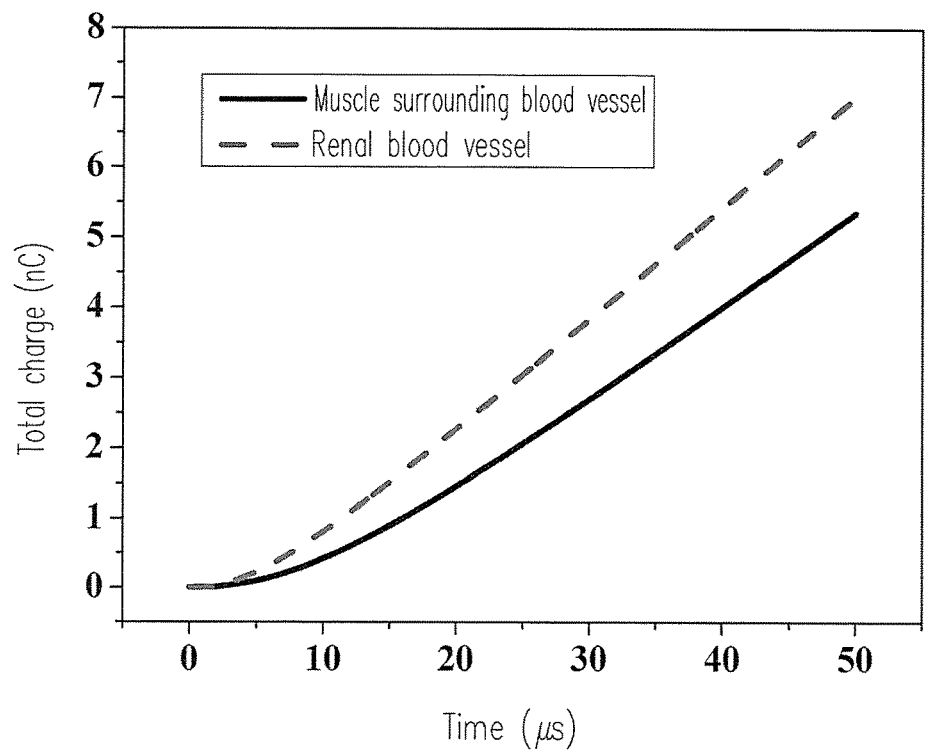
FIG. 7 is a diagram illustrating the relationship between charge and time of Example 2, so as to illustrate a curve diagram of current being integrated with respect to time of FIG. 6.
Figure 8:
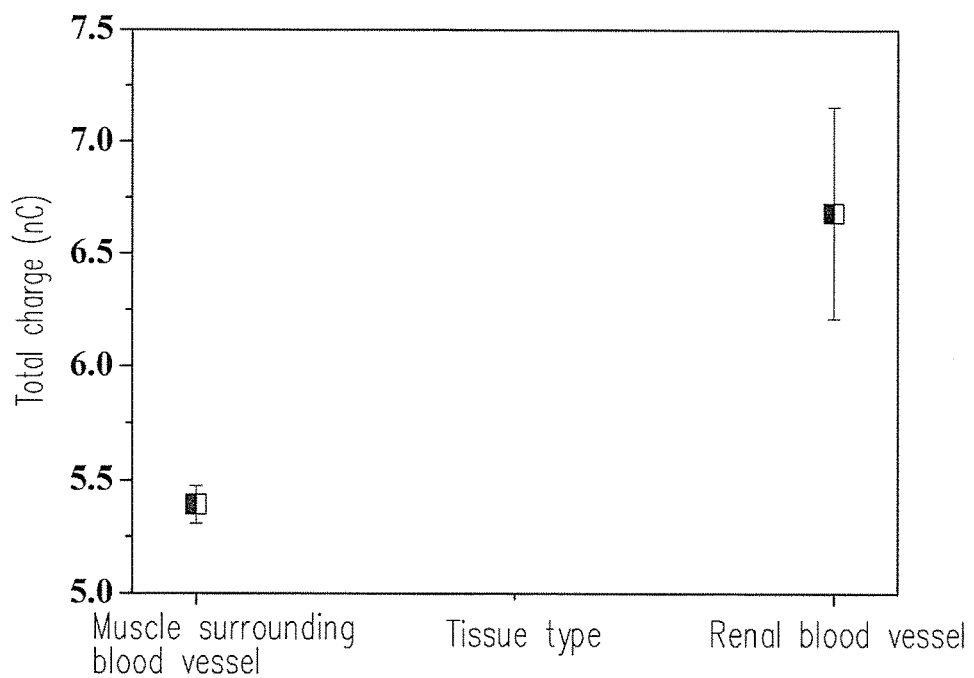
FIG. 8 is a diagram illustrating the relationship between specific time and charge of Example 2, so as to assist in illustrating the charge value at 50 s of FIG. 7.

FIG. 6 is a diagram illustrating the relationship between current and time obtained from the detection of the renal blood vessel sample and the muscle surrounding renal blood vessel sample by the tissue identification method of the invention in Example 2. FIG. 7 is a diagram illustrating the relationship between charge and time of Example 2, so as to illustrate a curve diagram of current being integrated with respect to time of FIG. 6. FIG. 8 is a diagram illustrating the relationship between specific time and charge of Example 2, so as to assist in illustrating the charge value at 50 µs of FIG. 7.

Referring to FIG. 6, within a time period of 50 µs, the detection currents (first sensing indicators) of the renal blood vessel sample and the muscle surrounding renal blood vessel sample are significantly different. Thus, the tissue identification method provided by the invention can identify and distinguish the renal blood vessel and the muscle surrounding renal blood vessel more effectively, simply and rapidly, so as to prevent surgeons from miscutting blood vessels during the surgical operation.

In addition to using the detection current I as the first sensing indicator, the second sensing indicator, in which the charge is used as an indicator, can be obtained by the transform step as described above.

Referring to FIG. 7, FIG. 7 shows a charge curve with respect to time obtained from an integral transform performed on each current value curve with respect to time of FIG. 6. From FIG. 7, within a time period of 50 µs, the total amounts of charge (second sensing indicators) of the renal blood vessel sample and the muscle surrounding renal blood vessel sample are significantly different. From the amount of charge being equal to the current times time (Q=I×t), it can be known that the amount of charge is proportional to the current. Thus, the charge curve shown in FIG. 7 conforms with the results of FIG. 6 in deed. Then, referring to FIG. 8, which shows the corresponding charge value at 50 µs for FIG. 7, the charge values of the renal blood vessel sample and the muscle surrounding renal blood vessel sample are significantly different.

Figure 9:
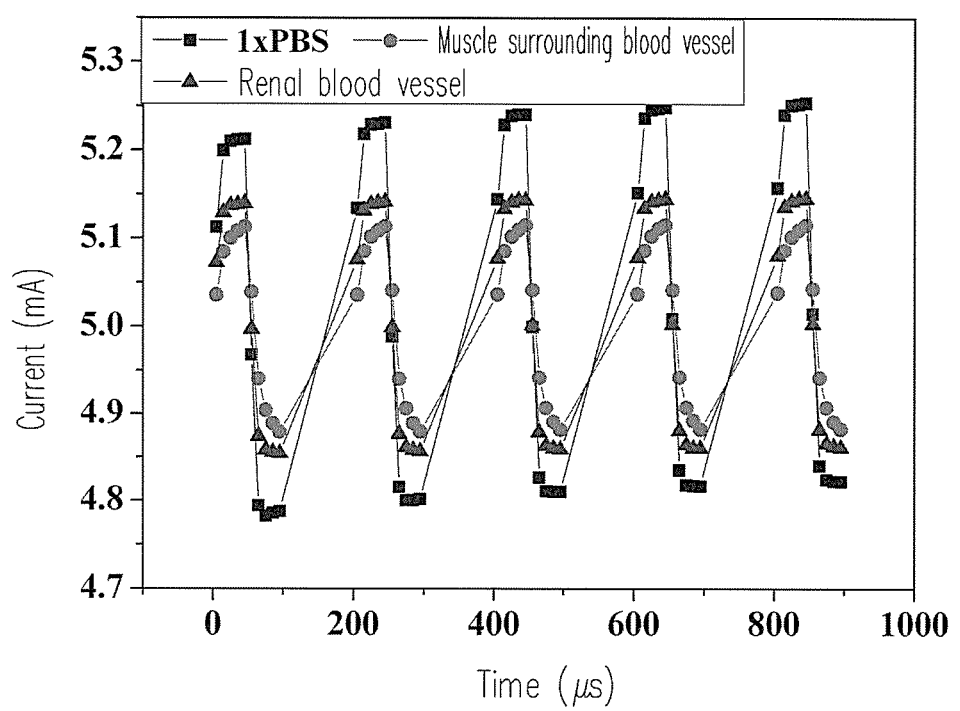
FIG. 9 is a diagram illustrating the relationship between current and time obtained from the detection of PBS, the renal blood vessel sample and the muscle surrounding renal blood vessel sample by the tissue identification method of the invention in Example 2.

FIG. 9 is a diagram illustrating the relationship between current and time obtained from the detection of PBS, the renal blood vessel sample and the muscle surrounding renal blood vessel sample by the tissue identification method of the invention in Example 2.

Referring to FIG. 9, within a time period of 1000 µs, the detection currents (first sensing indicators) of 1×PBS, the renal blood vessel sample and the muscle surrounding renal blood vessel sample are significantly different. Thus, it proves again that the tissue identification method provided by the invention can identify and distinguish the renal blood vessel and the muscle surrounding renal blood vessel more effectively, simply and rapidly, so as to prevent surgeons from miscutting blood vessels during the surgical operation.

In summary, the tissue identification method of the invention is performed by the high electron mobility transistor. The high electron mobility transistor has advantages of good electrical property, chemical stability, biological compatibility, thermal stability, and low power consumption. Thus, the tissue identification method can identify and distinguish tissue more effectively, simply and rapidly. The tissue identification method of the invention can be applied to the field related to the surgical medical operation, and the biosensor of the invention can be used as the auxiliary tool for the surgical medical operation (for example, the biosensor can be combined with surgical operation device (e.g., surgical knife)). As a result, the tissue identification method is able to prevent surgeons from miscutting blood vessels during the surgical operation. Also, it is able to prevent damage of normal tissue and resect the tumor tissue more effectively during the tumor tissue resection operation, thereby improving the efficiency and safety of the surgical medical operation.

Although the invention has been described with reference to the above embodiments, it will be apparent to one of ordinary skill in the art that modifications to the described embodiments may be made without departing from the spirit of the invention. Accordingly, the scope of the invention is defined by the attached claims not by the above detailed descriptions.

What is claimed is:

1. A tissue identification method, comprising:
   a preparation step of preparing a biosensor which comprises a transistor and a response electrode, wherein the response electrode is spaced apart from the transistor relative to a gate terminal of the transistor; and
   a detection step of disposing a biological tissue sample to be identified on the response electrode in a presence of a liquid medium, applying a pulse voltage which has a tunable pulse width and a tunable pulse height to the response electrode, resulting in a voltage difference between the response electrode and the gate terminal of the transistor, and measuring and calculating a detection current which is generated from the transistor in the pulse width so as to obtain a first sensing indicator, wherein a source of the biological tissue sample is muscles, blood vessels, tissues surrounding blood vessels, fats, viscera, or tumor tissues, a detection is performed on different biological tissue samples, and different first sensing indicators are obtained so as to identify and distinguish the different biological tissue samples.

2. The tissue identification method according to claim 1, further comprising performing a transform step after the detection step, wherein an integral transform is performed on the detection current with respect to the pulse width so as to obtain a second sensing indicator.

3. The tissue identification method according to claim 1, further comprising performing a transform step after the detection step, wherein a value of the detection current corresponding to the pulse width is divided by a maximum value of the detection current to obtain a dynamic current value, and an integral transform is performed on the dynamic current value with respect to the pulse width so as to obtain a third sensing indicator.

4. The tissue identification method according to claim 1, wherein the transistor comprises a high electron mobility transistor, a Si-based field-effect transistor, a nanowire field-effect transistor, a carbon nanotube field-effect transistor, a graphene field-effect transistor, or a molybdenum disulfide field-effect transistor.

5. The tissue identification method according to claim 1, wherein the response electrode is spaced apart on the gate terminal of the transistor.

6. The tissue identification method according to claim 1, wherein the response electrode is disposed on a substrate of the transistor, and the response electrode and the gate terminal of the transistor are arranged in a coplanar manner.

7. A biosensor for tissue identification, comprising:
   a transistor having a gate terminal; and
   a response electrode spaced apart from the transistor relative to the gate terminal of the transistor, and a biological tissue sample to be identified is disposed on the response electrode in a presence of a liquid medium,
   wherein when a pulse voltage which has a tunable pulse width and a tunable pulse height is applied to the response electrode, a voltage difference is generated between the response electrode and the gate terminal of the transistor, and a detection current which is generated from the transistor is measured and calculated in the pulse width so as to obtain a first sensing indicator,
   wherein a source of the biological tissue sample is muscles, blood vessels, tissues surrounding blood vessels, fats, viscera, or tumor tissues, a detection is performed on different biological tissue samples, and different first sensing indicators are obtained so as to identify and distinguish the different biological tissue samples.

8. The biosensor for tissue identification according to claim 7, wherein the transistor comprises a high electron mobility transistor, a Si-based field-effect transistor, a nanowire field-effect transistor, a carbon nanotube field-effect transistor, a graphene field-effect transistor, or a molybdenum disulfide field-effect transistor.

9. The biosensor for tissue identification according to claim 7, wherein the response electrode is spaced apart on the gate terminal of the transistor.

10. The biosensor for tissue identification according to claim 7, wherein the response electrode is disposed on a substrate of the transistor, and the response electrode and the gate terminal of the transistor are arranged in a coplanar manner.

\* \* \* \* \*